(12) United States Patent
Dwivedi et al.

(10) Patent No.: US 9,439,903 B2
(45) Date of Patent: Sep. 13, 2016

(54) PROCESS FOR THE PREPARATION OF AMORPHOUS IMATINIB MESYLATE

(71) Applicant: CADILA HEALTHCARE LIMITED, Ahmedabad, Gujarat (IN)

(72) Inventors: Shriprakash Dhar Dwivedi, Ahmedabad (IN); Kumar Kamlesh Singh, Ahmedabad (IN); Ganpant Dan Shimbu Charan, Ahmedabad (IN); Chetan Jayantibhai Vasava, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 21 days.

(21) Appl. No.: 14/059,971

(22) Filed: Oct. 22, 2013

(65) Prior Publication Data

US 2014/0121215 A1    May 1, 2014

(30) Foreign Application Priority Data

Oct. 25, 2012    (IN) .......................... 3100/MUM/2012

(51) Int. Cl.
*A61K 31/506*    (2006.01)
*A61K 45/06*    (2006.01)
*C07D 403/00*   (2006.01)

(52) U.S. Cl.
CPC ............. *A61K 31/506* (2013.01); *A61K 45/06* (2013.01)

(58) Field of Classification Search
CPC ... A61K 31/506; A61K 45/06; C07D 403/00
USPC ...................................... 514/252.18; 544/295
See application file for complete search history.

(56) References Cited

U.S. PATENT DOCUMENTS

| 5,521,184 | A | 5/1996 | Zimmermann |
| 6,894,051 | B1 | 5/2005 | Zimmermann et al. |
| 7,300,938 | B2 | 11/2007 | Parthasaradhi et al. |
| 7,947,699 | B2 * | 5/2011 | Khunt ................. C07D 401/04 424/464 |
| 7,974,699 | B2 | 7/2011 | Tano et al. |
| 8,048,883 | B2 | 11/2011 | Amala et al. |
| 8,269,003 | B2 | 9/2012 | Pathi et al. |
| 2008/0234286 | A1 | 9/2008 | Weisman et al. |
| 2010/0178336 | A1 | 7/2010 | Goncalves et al. |

FOREIGN PATENT DOCUMENTS

WO    2007/136510    * 11/2007

* cited by examiner

*Primary Examiner* — James O. Wilson
*Assistant Examiner* — Ebenezer O Sackey
(74) *Attorney, Agent, or Firm* — Ladas & Parry LLP

(57) ABSTRACT

The field of the invention relates to a process for the preparation of amorphous imatinib mesylate. In particular, the invention relates to a process for the preparation of stable amorphous imatinib mesylate. More particularly, the invention relates to pharmaceutical compositions that includes the stable amorphous imatinib messylate together along with its excipients.

11 Claims, 1 Drawing Sheet

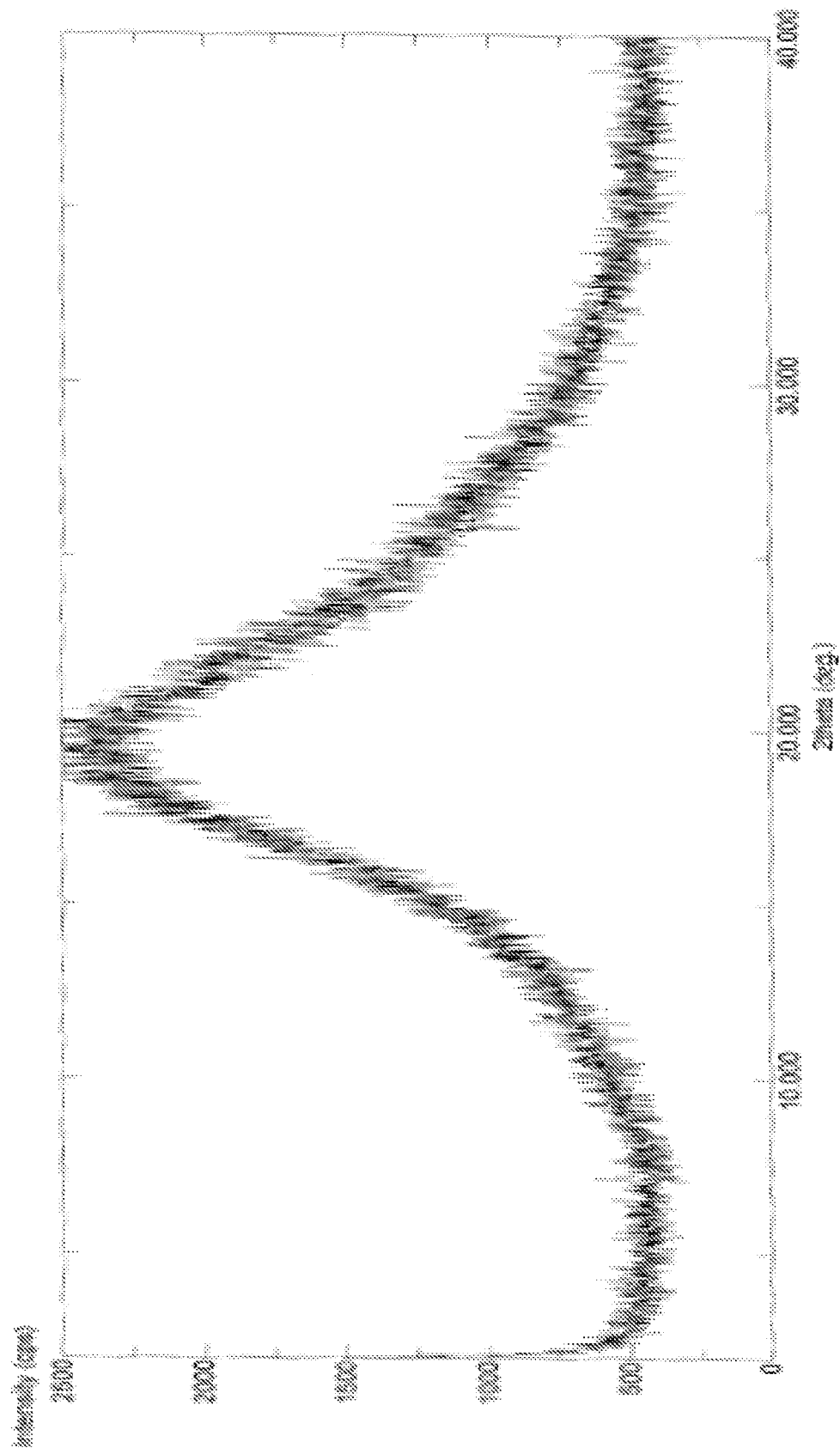

PROCESS FOR THE PREPARATION OF AMORPHOUS IMATINIB MESYLATE

FIELD OF THE INVENTION

The field of the invention relates to a process for the preparation of amorphous imatinib mesylate. In particular, the invention relates to a process for the preparation of stable amorphous imatinib mesylate. More particularly, the invention relates to pharmaceutical compositions that includes the stable amorphous imatinib mesylate together along with its excipients.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

Imatinib mesylate (CAS 220127-57-1) is a first generation tyrosine kinase inhibitor that is used in the treatment of chronic myelogenous leukemia (CML), gastrointestinal stromal tumors (GIST), and other cancers. It selectively targets certain tyrosine kinases, including c-ABL, and platelet-derived growth factor receptor. In CML, imatinib (mesylate) inhibits the oncoprotein BCR-ABL. It is available under the trade name of Gleevec™ for the treatment of Philadelphia chromosome positive chronic myeloid leukemia and malignant gastrointestinal stromal tumors (GIST). Gleevec film-coated tablets contain imatinib mesylate equivalent to 100 mg or 400 mg of imatinib free base.

It has been observed in many cases that amorphous form of the pharmaceutical products is known to have better dissolution properties than the crystalline forms. Hence, the present invention provides a process for the preparation of stable amorphous imatinib mesylate which is at least an useful alternative over the reported prior arts herein below.

U.S. Pat. No. 5,521,184 discloses a variety of N-Phenyl-2-Pyrimidine amine derivatives, process for their preparation, pharmaceutical composition and methods of use thereof. Among them Imatinib, which is chemically known as 4-[(4-Methyl-piperazinyl)methyl]-N-[4-methyl-3-[[4-(3-pyridinyl)-2-pyrimidinyl]amino]-phenyl]benzamide is a protein tyrosin kinase inhibitor. Imatinib is usually administered orally in the form of suitable salt, including Imatinib mesylate as represented by structural Formula I.

U.S. Pat. No. 6,894,051 B1 (the U.S. '051 patent) discloses α-crystal form and β-crystal form of Imatinib mesylate. The U.S. '051 patent in particular discloses non-needle-shaped crystals, especially the β-crystal form of the methane sulfonic acid addition salt of the compound of Formula I.

Indian patent application publications No. 1208/MUM/2003 and 1209/MUM/2003 disclose the γ-form of imatinib mesylate, which is amorphous in nature when characterized by x-ray powder diffraction pattern. The γ-form of imatinib mesylate is disclosed to have 1.5 to 5% of water content. The applications further disclose the process discloses the techniques of spray drying or freeze drying to obtain amorphous form. Alternatively, there is also disclosed the process for the preparation of amorphous form of imatinib mesylate by crystallizing from methanol and water mixture.

U.S. Pat. No. 7,300,938 B2 (the U.S. '938 patent) discloses a crystalline form H1, hydrate of imatinib mesylate and amorphous imatinib mesylate hydrate. The U.S. '938 patent also discloses the process for preparation of crystalline form H1, hydrate of imatinib mesylate and amorphous imatinib mesylate hydrate. The term hydrate in the U.S. '938 refers to the water content in the range of 2.0% to 3.2%.

U.S. Pat. No. 7,974,699 B2 (the U.S. '699 patent) discloses an amorphous form of imatinib mesylate having a water content of less than 0.5 percent by weight, based on the total weight of amorphous imatinib mesylate and process for its preparation.

U.S. Patent application publication No. 2008/0234286 A1 discloses stable micronized amorphous imatinib mesylate, having water content in the range of 3.2-5.0%, which is suitable for pharmaceutical compositions containing the amorphous imatinib mesylate. The reference example-1 discloses evaporation under vacuum at 50° C. to obtain residue as an oil which solidifies to a glassy deliquescent material upon long storage. The final water content, according to KF titration was 2.2% H₂O.

U.S. Patent application publication No. 2008/0234286 A1 in reference example 2 discloses the repetition of example 8 as per U.S. Pat. No. 7,300,938, wherein the solution of imatinib mesylate in a mixture of methanol and water was spray dried for 8 hours. The resulting viscous brown liquid was dried for additional 17 hours under vacuum at 50° C. The final water content according to KF titration was 1.7% H₂O. The spray dried material was very electrostatic and tended to agglomerate.

U.S. Patent application publication No. 2008/0234286 A1 itself discloses spray drying technique for the preparation of

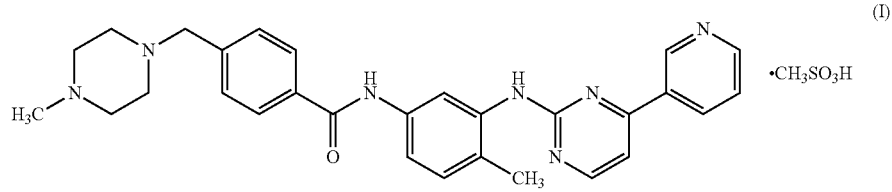

(I)

Imatinib mesylate can exist in different polymorphic forms, which differ from each other in terms of stability, physical properties, spectral data and the method of preparation. Various polymorphic forms, including hydrated and solvated forms of Imatinib mesylate designated forms α, β, H1, α2, δ, ε, I, II, F, G, H, I, K, IV, V, VI, VII, VIII, IX, X, XI, XIII, XIV, XV, XVI and amorphous form are apparently disclosed in various patents.

amorphous imatinib mesylate by use of water as a solvent and use of additives for stabilization of amorphous form.

U.S. Patent application publication No. 2010/0178336 A1 discloses a pharmaceutical composition comprising a stabilized amorphous imatinib mesylate as a complex with a cyclodextrin selected from β-cyclodextrin and hydroxypropyl β-cyclodextrin.

U.S. Pat. No. 8,048,883 B2 discloses a novel crystalline form α2 of imatinib mesylate, process for preparation of α2 crystalline form and pharmaceutical composition thereof.

U.S. Pat. No. 8,269,003 B2 describes the process for the preparation of alpha crystal form of imatinib mesylate, but did not provide any information on amorphous form of imatinib mesylate.

Therefore, one of the objectives of the present invention is to provide the convenient and industrially applicable method for preparation of imatinib mesylate amorphous form or at least which is a useful alternative over the cited prior arts.

In view of the above cited prior art, it is therefore, desirable to provide an efficient process for the preparation of amorphous form of imatinib mesylate. The present invention thereby provides useful alternative for the preparation of stable amorphous imatinib mesylate with substantial purity. Further, the present invention thereby further extends to the process for the preparation of imatinib mesylate amorphous form in essentially pure form.

SUMMARY OF THE INVENTION

In one general aspect, there is provided an amorphous imatinib mesylate having water content less than 2% wt/wt.

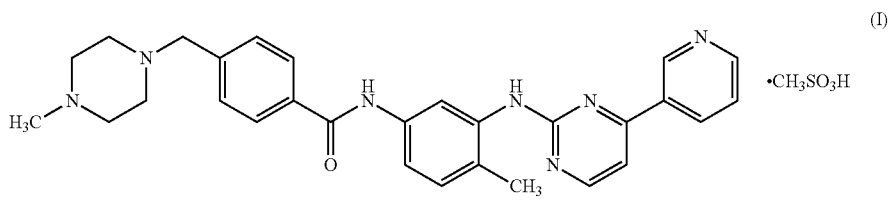

In another general aspect, there is provided an amorphous imatinib mesylate having water content in the range of 0.7% to 1.7% wt/wt.

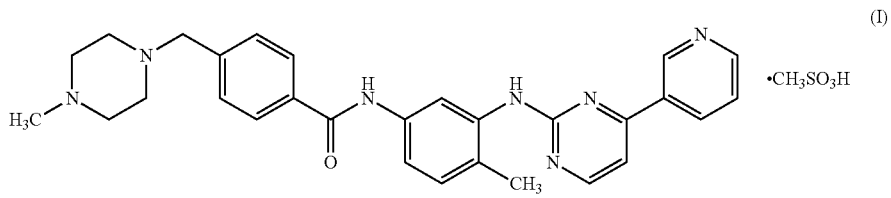

In another general aspect, there is provided a stable amorphous imatinib mesylate having water content less than 2% wt/wt in the range of 0.7% to 1.7% wt/wt.

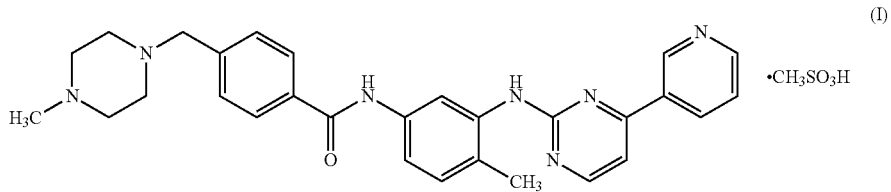

In another general aspect, there is provided a process for the preparation of stable amorphous imatinib mesylate of Formula (I)

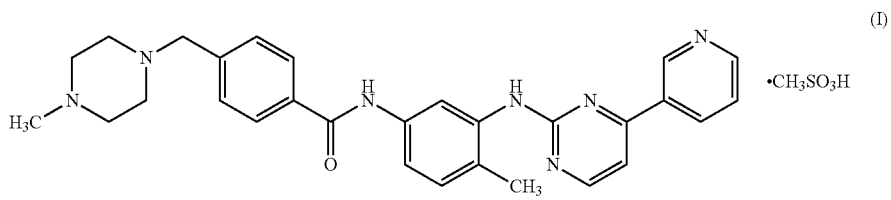

the process comprising:
(a) providing imatinib free base of Formula (II) in one or more of suitable organic solvent to obtain reaction mixture;
(b) adding methane sulfonic acid to the reaction mixture;
(c) adding water to the reaction mixture to obtain imatinib mesylate;
(d) removal of organic solvent to obtain residue;
(e) treating the residue with ethereal anti-solvent to obtain amorphous imatinib mesylate; and
(f) drying at 60° C. under vacuum for sufficient time to obtain stable amorphous imatinib mesylate.

In another general aspect, there is provided a process for the preparation of stable amorphous imatinib mesylate of Formula (I)

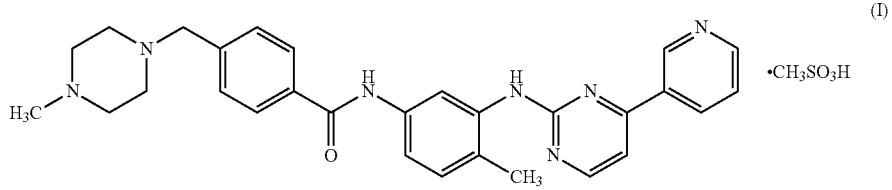

the process comprising:
(a) providing imatinib free base of Formula (II) in mixture of alcohol and chlorinated solvents to obtain reaction mixture;
(b) adding methane sulfonic acid to the reaction mixture;
(c) adding water to the reaction mixture to obtain imatinib mesylate;
(d) removal of organic solvent to obtain residue;
(e) treating the residue with methyl tert-butyl ether to obtain amorphous imatinib mesylate; and
(f) drying at 60° C. under vacuum for sufficient time to obtain stable amorphous imatinib mesylate.

In another general aspect, there is provided essentially pure amorphous imatinib mesylate having water content in the range of 0.7% to 1.7% wt/wt.

In another general aspect, there is provided a pharmaceutical composition comprising a therapeutically effective amount of amorphous imatinib mesylate having water content in the range of 0.7% to 1.7% wt/wt and one or more pharmaceutically acceptable diluents or carriers, excipients, or diluents and, optionally one or more other physiologically active agents.

BRIEF DESCRIPTION OF DRAWINGS

FIG. 1: Graph illustrating Powder X-ray Diffraction pattern of amorphous Imatinib mesylate.

DETAILED DESCRIPTION OF THE INVENTION

The prior art discloses the amorphous imatinib mesylate having water content in the range of 2.0 to 3.2% or 3.5% to 5.0% along with its stability. The present inventors provide a process for the preparation of amorphous imatinib mesylate having water content less than 2.0%, in particular in the range of 0.7% to 1.7% wt/wt. Further, the invention also provides essentially pure amorphous imatinib mesylate. The purity of imatinib is measured in terms of impurity profile. The amorphous imatinib mesylate prepared by the process of the present invention is having purity of about 99.9% or more. In particular, there is no detectable amount of oxides of imatinib.

The present invention can comprise (open ended) or consist essentially of the components of the present invention as well as other ingredients or elements described herein. As used herein, "comprising" means the elements recited, or their equivalent in structure or function, plus any other element or elements which are not recited. The terms "having" and "including" are also to be construed as open ended unless the context suggest otherwise.

As used here in the term "obtaining" may include filtration, filtration under vacuum, centrifugation, and decantation. The product obtained may be further or additionally dried to achieve the desired moisture values. For example, the product may be dried in a tray drier, dried under vacuum and/or in a Fluid Bed Drier.

All ranges recited herein include the endpoints, including those that recite a range "between" two values. Terms such as "about", "general", "essentially" and the like are to be construed as modifying a term or value such that it is not an absolute. This includes, at very least, the degree of expected experimental error, technique error and instrument error for a given technique used to measure a value.

The term "essentially pure" means stable amorphous imatinib mesylate containing less than about 0.1% (wt/wt) any single individual impurities like N-oxide, Di-N-oxide, 4-[(4-methylpiperazin-1-yl)methyl]benzoic acid (MP-MBA), N-(5-amino-2-methylphenyl)-4-(3-pyridyl)-2-pyrimidine-amine (AMPPP), Methyl 4-((4-methylpiperazin-1-yl)methyl)benzoate (Methyl Ester analouge), N-(2-Methyl-5-nitrophenyl)-4-(pyridin-3-yl)pyrimidin-2-amine (NMPPP) when measured by area percentage of HPLC.

The essentially pure amorphous imatinib mesylate having less than about 0.1% of single individual impurities and N-oxide or Di-N-oxide not in detectable amount when measured by area percentage of HPLC.

The term "suitable solvent" means a single or a combination of two or more solvents.

The term "stable" refers to amorphous imatinib mesylate having less than 2.0% water, in particular, having less than 1.7% water, more particularly, water content is in the range of 0.7% to 1.7% wt/wt when stored at 25° C./60% RH or at about 40° C./75% RH for at least 6 months.

The prior arts U.S. Patent application publication Nos. 2008/0234286 A1 and 2010/0178336 A1 discloses use of additives or cyclodextrin for stabilization of amorphous form of imatinib mesylate.

The present invention provides a process for the preparation of amorphous imatinib mesylate having water content less than 2% wt/wt. In particular, a stable amorphous imatinib mesylate having water content in the range of 0.7% to 1.7% wt/wt wherein there is no usage of additive or excipients or stabilizers.

In one general aspect, the amorphous imatinib mesylate was subjected to study the hygroscopicity as per the Ph. Eur. general chapter 5.11. Based on the hygroscopicity performed with respect to the amorphous imatinib mesylate, it was observed that the amorphous imatinib mesylate was very hygroscopic in nature as per EP. Therefore, the amorphous imatinib mesylate tends to absorb moisture rapidly as it is very hygroscopic in nature.

The amorphous imatinib mesylate having less than 2.0% water, in particular, having less than 1.7% water, more particularly, water content is in the range of 0.7% to 1.7% as manufactured by the process of the present invention was subjected to stability for at least 6 months at 25° C./60% RH or at about 40° C./75% RH. The following Table-1 and Tabel-2 discloses the stability conditions and results.

TABLE 1

| | Packaging condition | Packed in double poly bag with molecular sieve pillow pack under Nitrogen as a primary packaging and this bag is further protected with triple laminated aluminum bag with silica gel pillow pack under Nitrogen and kept in HDPE drum | | | |
|---|---|---|---|---|---|
| | Storage condition | 25° C. ± 2° C./60% ± 5% RH (Real time) | | | |

| Sr. No. | Test | Specification | 1 Month | 2 Months | 3 Months | 6 Months |
|---|---|---|---|---|---|---|
| 1. | Description | Pale yellow to yellow powder | Pale yellow powder | Pale yellow powder | Pale yellow powder | Pale yellow powder |
| 2. | X-Ray Diffraction | The X-ray diffractogram should confirm the amorphous | Amorphous | Amorphous | Amorphous | Amorphous |
| 3. | Water (%) | Less than 2% w/w | 0.72 | 0.64 | 0.65 | 0.69 |
| 4. | | Related substance (%) by HPLC | | | | |
| | Impurity-MPMBA | NMT 0.1 w/w | BQL | BQL | BQL | BQL |
| | Impurity-AMPPP | NMT 0.1 w/w | BQL | BQL | BQL | BQL |
| | Impurity-Methyl Ester analouge | NMT 0.1 w/w | BQL | BQL | BQL | BQL |
| | Impurity-NMPPP | NMT 0.1 w/w | BQL | BQL | BQL | BQL |
| | Single largest unknown Imp | NMT 0.10 w/w | 0.03 | 0.03 | 0.03 | 0.03 |
| | Total Impurities | NMT 0.5 w/w | 0.04 | 0.04 | 0.05 | 0.06 |

BQL = Below Quantification Limit

TABLE 2

| | Packaging condition | Packed in double poly bag with molecular sieve pillow pack under Nitrogen as a primary packaging and this bag is further protected with triple laminated aluminum bag with silica gel pillow pack under Nitrogen and kept in HDPE drum | | | |
|---|---|---|---|---|---|
| | Storage condition | 40° C. ± 2° C./75% ± 5% RH (Accelerated) | | | |

| Sr. No. | Test | Specification | 1 Month | 2 Month | 3 Month | 6 Month |
|---|---|---|---|---|---|---|
| 1. | Description | Pale yellow to yellow powder | Pale yellow powder | Pale yellow powder | Pale yellow powder | Pale yellow powder |
| 2. | X-Ray Diffraction | The X-ray diffractogram should confirm the amorphous | Amorphous | Amorphous | Amorphous | Amorphous |
| 3. | Water (%) | Less than 2% w/w | 0.88 | 0.89 | 0.79 | 0.95 |
| 4. | | Related substance (%) by HPLC | | | | |
| | Impurity-MPMBA | NMT 0.1 w/w | BQL | BQL | BQL | BQL |
| | Impurity-AMPPP | NMT 0.1 w/w | BQL | BQL | BQL | BQL |
| | Impurity-Methyl Ester analouge | NMT 0.1 w/w | BQL | BQL | BQL | BQL |
| | Impurity-NMPPP | NMT 0.1 w/w | BQL | BQL | BQL | BQL |

TABLE 2-continued

| | | | | | |
|---|---|---|---|---|---|
| Single largest unknown Imp | NMT 0.10 w/w | 0.03 | 0.03 | 0.03 | 0.03 |
| Total Impurities | NMT 0.5 w/w | 0.04 | 0.05 | 0.07 | 0.07 |

BQL = Below Quantification Limit

In one general aspect, there is provided an amorphous imatinib mesylate having water content less than 2% wt/wt.

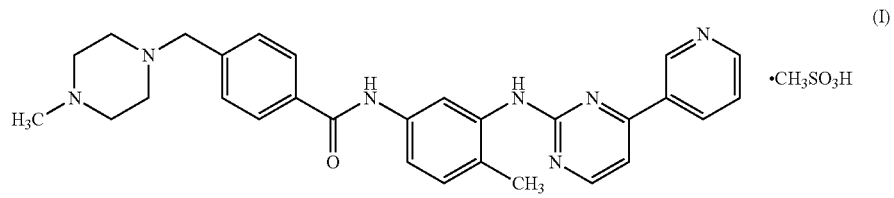

(I)

In general, the amorphous imatinib mesylate is having water content less than 1.7%. In particular, the water content is in the range of 0.7% to 1.7% wt/wt.

In another general aspect, there is provided an amorphous imatinib mesylate having water content in the range of 0.7% to 1.7% wt/wt.

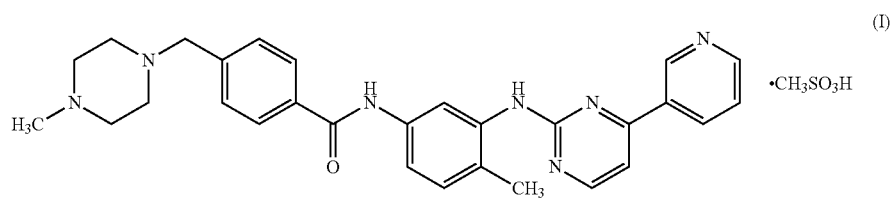

(I)

In another general aspect, there is provided a stable amorphous imatinib mesylate having water content less than 2% wt/wt in the range of 0.7% to 1.7% wt/wt.

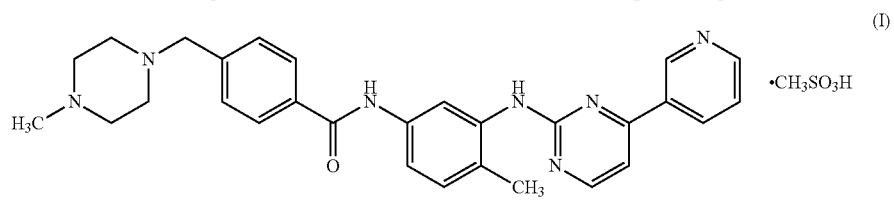

(I)

In another general aspect, there is provided an essentially pure amorphous imatinib mesylate.

In general, the essentially pure amorphous imatinib mesylate contains less than about 0.1% of N-oxide, Di-N-oxide, MPMBA, AMPPP, Methyl ester analouge and NMPPP impurities when measured by area percentage of HPLC. In particular, the stable amorphous imatinib mesylate of Formula (I) contains said impurities below quantification limits (BQL) when measured by area percentage of HPLC and N-oxide or Di-N-oxide not in detectable amount by area percentage of HPLC.

The imatinib free base of Formula (II) is used as the starting compound may be prepared by the process as disclosed in U.S. Pat. No. 5,521,184 and reaction scheme-1 herein after, which is incorporated herein by reference in its entirety.

In another general aspect, there is provided a process for the preparation of stable amorphous imatinib mesylate of Formula (I)

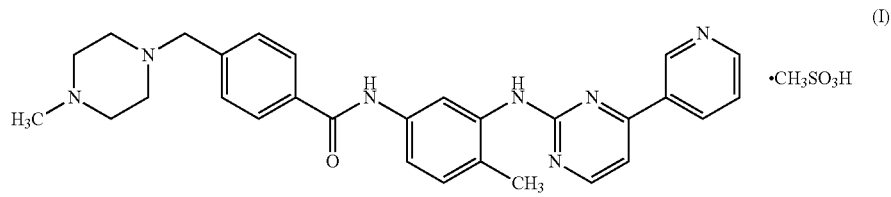

(I)

the process comprising:
(a) providing imatinib free base of Formula (II) in one or more of suitable organic solvent to obtain reaction mixture;
(b) adding methane sulfonic acid to the reaction mixture;
(c) adding water to the reaction mixture to obtain imatinib mesylate;
(d) removal of organic solvent to obtain residue;
(e) treating the residue with ethereal anti-solvent to obtain amorphous imatinib mesylate; and
(f) drying at 60° C. under vacuum for sufficient time to obtain stable amorphous imatinib mesylate.

In general, the suitable organic solvent comprises one or more of alcohols like water, alcohols, ketones, nitriles, amides, esters, halogenated hydrocarbons. In particular, the suitable organic solvent comprises one or more of water, methanol, ethanol, isopropanol, n-butanol, acetone, methyl ethyl ketone, methyl isobutyl ketone, acetonitrile, dimethyl formamide, dimethyl acetamide, dimethyl sulfoxide, N-methylpyrrolidone, ethyl acetate, isopropyl acetate, butyl acetate, dichloromethane, dichloroethane, chloroform, chlorobenzene, and the like. In particular, the suitable organic solvent may be a mixture of methanol and dichloromethane.

The embodiments of the process includes providing the solution of imatinib free base in methanol and dichloromethane at 25° C. The reaction mixture was treated with methane sulfonic acid followed by water to obtain imatinib mesylate salt. The reaction mixture was heated at 40° C. to 70° C. and concentrated to obtain residue. The residue was treated with suitable anti-solvent to obtain amorphous imatinib mesylate. The obtained amorphous imatinib mesylate may be dried at 60° C. under vacuum for sufficient time to obtain stable amorphous imatinib mesylate.

The sufficient time herein means drying amorphous imatinib mesylate for at least 5 hours, in particular for at least 10 hours.

In general, the suitable anti-solvent comprises one or more of diisopropyl ether, diethyl ether, methyl tert-butyl ether, tetrahydrofuran, 1,4-dioxane and the like. In particular, methyl tert-butyl ether may be used.

In another general aspect, there is provided a process for the preparation of amorphous imatinib mesylate of Formula (I)

the process comprising:
(a) providing imatinib free base of Formula (II) in mixture of alcohol and chlorinated solvents to obtain reaction mixture;
(b) adding methane sulfonic acid to the reaction mixture;
(c) adding water to the reaction mixture to obtain imatinib mesylate;
(d) removal of organic solvent to obtain the residue;
(e) treating the residue with methyl tert-butyl ether to obtain amorphous imatinib mesylate; and
(f) drying at 60° C. under vacuum for sufficient time to obtain stable amorphous imatinib mesylate.

In another general aspect, there is provided essentially pure amorphous imatinib mesylate having water content in the range of 0.7% to 1.7% wt/wt.

In another general aspect, there is provided a pharmaceutical composition comprising a therapeutically effective amount of stable amorphous imatinib mesylate having water content in the range of 0.7% to 1.7% wt/wt and one or more pharmaceutically acceptable diluents or carriers, excipients, and optionally one or more other physiologically active agents.

In another general aspect, there is a pharmaceutical composition comprising a therapeutically effective amount of stable amorphous imatinib mesylate having water content in the range of 0.7% to 1.7% wt/wt together with one or more pharmaceutically acceptable carriers, excipients or diluents and use thereof for the treatment of chronic myelogenous leukemia (CML), gastrointestinal stromal tumors (GIST), and other cancers.

The invention also encompasses pharmaceutical compositions comprising stable amorphous imatinib mesylate of the invention. As used herein, the term "pharmaceutical compositions" includes tablets, pills, powders, liquids, suspensions, emulsions, granules, capsules, suppositories, or injection preparations.

Pharmaceutical compositions containing the stable amorphous imatinib mesylate of the invention may be prepared by using diluents or excipients such as fillers, bulking agents, binders, wetting agents, disintegrating agents, surface active agents, and lubricants. Various modes of administration of the pharmaceutical compositions of the invention may be selected depending on the therapeutic purpose, for example tablets, pills, powders, liquids, suspensions, emulsions, granules, capsules, suppositories, or injection preparations.

In another general aspect, there is provided stable amorphous imatinib mesylate of Formula (I) having a HPLC purity of greater than about 98%, or greater than about 99%, or greater than about 99.5%, or greater than about 99.8%, or

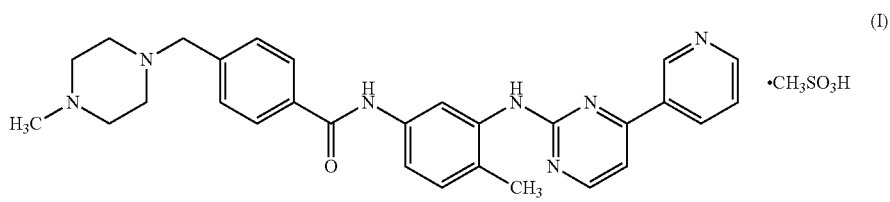

greater than about 99.9%, as determined using high performance liquid chromatography (HPLC).

In another general aspect, there is provided an improved process for the preparation of amorphous imatinib mesylate of Formula (I) according the reaction scheme-1 substantially as depicted herein after.

Scheme-1

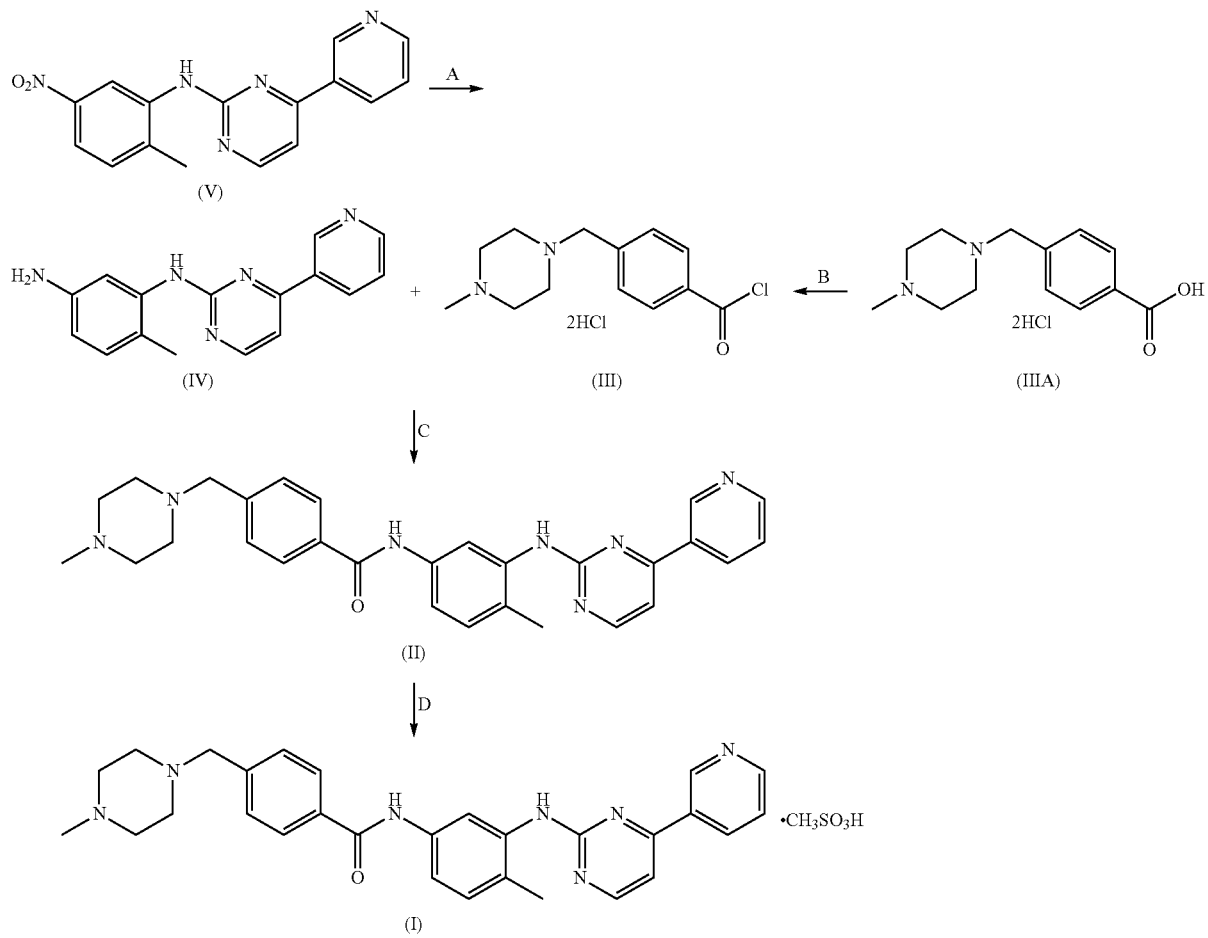

A. Pd/C, HCOONH₄;
B. SOCl₂;
C. Py, MDC, RT;
D. CH₃SO₃H, MeOH, MDC, MTBE.

Having described the invention with reference to certain preferred embodiments, other embodiments, reaction conditions, temperature control and solvent system may become apparent to one skilled in the art from consideration of the examples provided herein after. The examples are provided as one of the possible way to practice the invention and should not be considered as limitation of the scope of the invention.

EXAMPLES

Example-1

Preparation of Imatinib Mesylate Amorphous Form

Imatinib free base (90 g), methanol (450 mL) and dichloromethane (270 mL) were stirred at 25° C. in round bottom flask in presence of nitrogen. Methanesulfonic acid (18 g) was slowly added to the reaction mixture at 25° C. Water (27 mL) was added and the reaction mixture was stirred for 2 hours. The reaction mixture was heated at 50° C. and concentrated to remove the solvent mixture. The residue was degassed at 60° C. and cooled to 25° C. Methyl tert-butyl ether (630 mL) was added to the reaction mixture and stirred for 45 minutes. The product was filtered and washed with methyl tert-butyl ether. The product was dried at 60° C. under high vacuum for 10 hours to obtain amorphous imatinib mesylate. Water content 0.90%.

While the present invention has been described in terms of its specific embodiments, certain modifications and equivalents will be apparent to those skilled in the art and are intended to be included within the scope of the present invention.

We claim:

1. An amorphous imatinib mesylate of Formula (I)

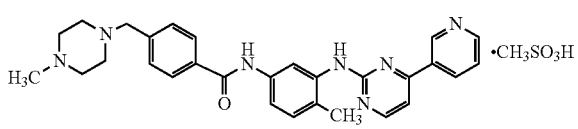

(I)

wherein the imatinib mesylate has a water content in the range of from 0.7% to 1.7% wt/wt and has an X-ray powder diffraction pattern substantially the same as that shown in FIG. 1 of the drawing.

2. The amorphous imatinib mesylate according to claim 1, wherein the imatinib mesylate is essentially pure having a purity greater than about 99.5% by area percentage of HPLC.

3. The amorphous imatinib mesylate according to claim 2, wherein the imatinib mesylate contains less than about 0.10% of any single individual impurity by area percentage of HPLC.

4. A pharmaceutical composition comprising a therapeutically effective amount of the amorphous imatinib mesylate according to claim 1 and one or more selected from the group consisting of a pharmaceutically acceptable diluent, carrier and excipient.

5. The amorphous imatinib mesylate according to claim 2, wherein the imatinib mesylate is essentially pure having no detectable amount of N-oxide or Di-N-oxide impurities by area percentage of HPLC.

6. The amorphous imatinib mesylate according to claim 1, which is stable and remains amorphous when stored at a temperature of 25° C. at a Relative Humidity of 60% or at a temperature of 40° C. at a Relative Humidity of 75% for at least 6 months.

7. The amorphous imatinib mesylate according to claim 1, which is stable and retains its water content in the range of from 0.7% to 1.7% wt/wt when stored at a temperature of 25° C. at a Relative Humidity of 60% or at a temperature of 40° C. at a Relative Humidity of 75% for at least 6 months.

8. A process for the preparation of the amorphous imatinib mesylate according to claim 1, the process comprising:
(a) providing an imatinib free base of Formula (II),

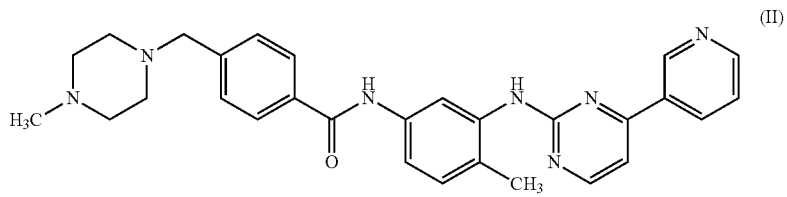 [SMILES: Cc1ccc(NC(=O)c2ccc(CN3CCN(C)CC3)cc2)cc1Nc1nccc(-c2cccnc2)n1]

in one or more solvents to obtain a reaction mixture;
(b) adding methane sulfonic acid to the reaction mixture;
(c) adding water to the reaction mixture;
(d) removing the solvent to obtain a residue;
(e) treating the residue with an ethereal anti-solvent to obtain the imatinib mesylate; and
(f) drying at 60° C. under vacuum for a sufficient time to obtain the amorphous imatinib mesylate.

9. The process according to claim 8, wherein the solvent is selected from the group consisting of one or more of water, methanol, ethanol, isopropanol, n-butanol, acetone, methyl ethyl ketone, methyl isobutyl ketone, acetonitrile, dimethyl formamide, dimethyl acetamide, dimethyl sulfoxide, N-methyl pyrrolidone, ethyl acetate, isopropyl acetate, butyl acetate, dichloromethane, dichloroethane, chloroform, chlorobenzene and a mixture thereof.

10. The process according to claim 8, wherein the solvent is a mixture of methanol and dichloromethane.

11. The process according to claim 8, wherein the ethereal anti-solvent is selected from the group consisting of one or more of diisopropyl ether, diethyl ether, methyl tert-butyl ether, tetrahydrofuran and 1,4-dioxane.

* * * * *